US006578581B1

(12) United States Patent
Khalsa

(10) Patent No.: US 6,578,581 B1
(45) Date of Patent: Jun. 17, 2003

(54) METHOD AND APPARATUS FOR RELIEVING FLUID BUILD-UP IN THE MIDDLE EAR

(76) Inventor: Siri Nam Khalsa, 26600 S. Canoa Rd., Amado, AZ (US) 85645

( * ) Notice: Subject to any disclaimer, the term of this patent is extended or adjusted under 35 U.S.C. 154(b) by 0 days.

(21) Appl. No.: 09/682,491

(22) Filed: Sep. 7, 2001

Related U.S. Application Data

(60) Provisional application No. 60/232,306, filed on Sep. 12, 2000.

(51) Int. Cl.[7] ................................................ A61F 11/00
(52) U.S. Cl. ......................... 128/898; 606/169; 604/514
(58) Field of Search .................. 601/76, 2, 4; 128/97.1, 128/898; 604/19, 22, 35, 540–543, 514; 606/108, 109, 167, 169, 185, 127, 128, 168

(56) References Cited

U.S. PATENT DOCUMENTS

| 4,024,866 | A | * | 5/1977 | Wallach | 604/172 |
|---|---|---|---|---|---|
| 4,258,714 | A | | 3/1981 | Leopoldi et al. | |
| 4,403,611 | A | | 9/1983 | Babbitt et al. | |
| 4,428,748 | A | * | 1/1984 | Peyman et al. | 433/119 |
| 4,684,362 | A | | 8/1987 | Holt | |
| 5,114,415 | A | | 5/1992 | Shedlock | |
| 5,513,627 | A | | 5/1996 | Flam | |
| 5,514,086 | A | * | 5/1996 | Parisi et al. | 601/2 |
| 5,665,080 | A | | 9/1997 | Vandenberg | |
| 5,741,269 | A | | 4/1998 | McCredy | |
| 5,911,699 | A | * | 6/1999 | Anis et al. | 604/22 |
| 5,916,150 | A | | 6/1999 | Sillman | |
| 5,928,190 | A | | 7/1999 | Davis | |
| 6,024,726 | A | | 2/2000 | Hill | |
| 6,059,803 | A | | 5/2000 | Spilman | |
| 6,221,006 | B1 | * | 4/2001 | Dubrul et al. | 600/159 |
| 6,245,091 | B1 | * | 6/2001 | Buncke | 606/222 |

* cited by examiner

Primary Examiner—Danton D. DeMille
Assistant Examiner—Quang D. Thanh
(74) Attorney, Agent, or Firm—McGarry Bair PC

(57) ABSTRACT

A device and method are provided for clearing obstructions in a body cavity opening behind which a volume of fluid has been accumulated comprising a housing having a longitudinal internal conduit having an end interconnected to a suction source and a motor mechanically interconnected to a second end attachment portion and adapted to impart vibratory movement thereto. Actuation of the motor imparts vibratory movement to the second end attachment portion, and thereby to an attached tip and, when a housing first attachment portion is interconnected to a suction source, suction and vibration are simultaneously applied to the tip second end. Thus, when the tip second end is applied against an obstructed body cavity opening, the vibration acts to break up the obstruction and the suction contemporaneously acts to withdraw the accumulated fluid from the body cavity.

3 Claims, 11 Drawing Sheets

METHOD AND APPARATUS FOR RELIEVING FLUID BUILD-UP IN THE MIDDLE EAR

CROSS REFERENCE TO RELATED APPLICATIONS

This application claims the benefit of U.S. Provisional Application No. 60/232,306, filed Sep. 12, 2000.

BACKGROUND OF INVENTION

1. Field of the Invention

This invention relates to an apparatus and a method for draining the eustachian tube and middle ear of fluid when there is a blockage of the opening of the eustachian tube in the nasopharynx region of the throat.

2. Related Art

Referring to FIGS. 1–2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a eustachian tube 26 which serves as a pressure equalizing valve between the ear 10 and the sinuses. The eustachian tube 26 terminates in a distal opening 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34–38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The eustachian tube 26 is a narrow, one-and-a-half inch long channel connecting the middle ear 14 with the nasopharynx 30, the upper throat area just above the palate, in back of the nose. The eustachian tube 26 functions as a pressure equalizing valve for the middle ear 14 which is normally filled with air. When functioning properly, the eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the eustachian tube 26 may result in hearing impairment or other ear symptoms.

Obstruction or blockage of the eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition we call serous otitis media (fluid in the middle ear). This occurs frequently in children in connection with an upper respiratory infection and accounts for the hearing impairment associated with this condition.

A lining membrane (mucous membrane) of the middle ear 14 and eustachian tube 26 is connected with, and is the same as, the membrane of the nose 42, sinuses 44 and throat 32. Infection of these areas results in mucous membrane swelling which in turn may result in obstruction of the eustachian tube 26. This is referred to as serous otitis media, i.e., essentially a collection of fluid in the middle ear 14 that can be acute or chronic, usually the result of blockage of the distal opening 28 of the eustachian tube 26 which allows fluid to accumulate in the middle ear 14. In the presence of bacteria, this fluid may become infected leading to an acute suppurative otitis media (infected or abscessed middle ear). When infection does not develop, the fluid remains until the eustachian tube 26 again begins to function normally, at which time the fluid is absorbed or drains down the tube into the throat 32 through the eustachian tube opening 28.

Chronic serous otitis media may result from longstanding eustachian tube blockage, or from thickening of the fluids so that it cannot be absorbed or drained down the eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the eustachian tube 26 contains a build-up of fluid, a number of things will occur. First, the body absorbs the air from the middle ear 14, causing a vacuum to form which tends to pull the lining membrane and ear drum 22 inward causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected which is painful and makes the patient feel ill and may not be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14, i.e., the most immediate relief will be felt by the patient if the fluid can be removed from the eustachian tube 26.

Antibiotic treatment of middle ear infections typically result in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to insure ventilation of the middle ear 14. The ventilation tube 44 temporarily takes the place of the eustachian tube 26 in equalizing the pressure in the middle ear 14. The ventilation tube 44 usually remains in place for three to nine months during which time the eustachian tube 26 blockage subsides. When the tube 44 dislodges, the eardrum 22 heals; the eustachian tube 26 then resumes its normal pressure equalizing function.

Another method of relieving the pressure in the middle ear 14 is shown in FIG. 4 in which a hypodermic needle 46 is driven through the eardrum 22 through which any accumulated fluid can be withdrawn from typically only the upper portion of the eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the eustachian tube 26 since often the lower end 28 thereof is blocked and dammed with fluid.

In connection with the above surgical treatments of FIGS. 3 and 4, eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the eustachian tube 26 in the nasopharynx region 30 of the throat 32. Air is blown through the tip 48 via the syringe 46 into the obstructed eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This forces air into the eustachian tube 26 and the middle ear 14. This technique is good for opening the eustachian tube 26 but it does not clear accumulated fluid away.

Another method for clearing the middle ear 14 (at least temporarily) is referred to as the "valsalva" maneuver accomplished by forcibly blowing air into the middle ear 14 while holding the nose, often called popping the ear. This method is also good for opening the eustachian tube 26 but it does not clear the accumulated fluid away either.

Physicians in alternative medicine have had success draining the eustachian tube and middle ear by inserting a finger 50 into the back of the throat 32 and massaging the opening 28 of the eustachian tube 26 for a predetermined period of time. This seems to unblock the opening 28, allowing the eustachian tube 26 to drain down the throat 32 into the patient's esophagus—thus, this method also does not clear the accumulated fluid.

Thus, the prior art methods for relieving the pain of the build-up of fluid caused by middle ear 14 infections all fall short by not providing a convenient method to both unobstruct the blocked eustachian tube 26 opening 28 and to simultaneously clear away the accumulated fluid as it drains from the suddenly-opened opening 28 of the eustachian tube 26.

SUMMARY OF INVENTION

The device of the present invention consists of an attachment to a medical suction unit which consists of a handle with controls and a rigid tube that has a curve in it to reach the opening of the eustachian tube from the mouth. The semi rigid tube can be either disposable or non-diposable and can be made in different sizes. The end of the tube may be nobbed for rubbing against the opening of the eustachian tube. The handle has controls for the suction, lighting, a spray device for medications, visualization, and vibration. The handle could also have no controls, with the controls being with the main unit. The device can also be made without a handle, if only suction is required. In another embodiment, there is only a handle with vibration and other features but no suction.

The method consists of inserting the device, with or without a pre-spray of topical anesthesia, through the open mouth and into the pharynx. With the help of the curve in the tube the tip of the device may be placed against or adjacent to the opening of the eustachian tube. If optics are used for visualization, this helps to guide the end of the device into place. The light source attached to the device also aids in this procedure, but a separate light source may also be used. Once the device is in position, treatment consists of either suction of secretions, or vibration, or both. The procedure may be repeated several times if necessary. As the opening of the eustachian tube begins functioning properly, suction may be applied directly into the eustachian tube to clear the fluid there, or the fluid may be allowed to drain freely. At any time during the procedure or afterwards, medications may be sprayed directly onto the walls of the phayrnx or on the opening of the eustachian tube.

This method is better than previous technology because it is more effective at opening the eustachian tube and simulataneously collecting fluids draining from the suddenly-opened eustachian tube and far less invasive and permanently destructive than prior surgical methods.

In one aspect, the invention relates to a device for clearing obstructions in a body cavity opening behind which a volume of fluid has been accumulated comprising: a housing having a longitudinal internal conduit, the internal conduit terminating at a first end and a second end, the first and second ends having attachment portions thereon, the attachment portion at the first end being adapted to be interconnected to a suction source; a motor mechanically interconnected to the second end attachment portion and adapted to impart vibratory movement to the second end attachment portion; an elongated tip having a first end and a second end, each of the first and second ends having an opening therein, the tip having a longitudinal internal conduit extending between the openings in the first and second ends of the tip, the first end of the tip being mounted to the attachment portion at the housing second end wherein the internal conduit of the tip is in fluid communication with the longitudinal conduit of the housing; whereby actuation of the motor imparts vibratory movement to the second end attachment portion, and thereby to the attached tip and, when the housing first attachment portion is interconnected to a suction source, suction and vibration are simultaneously applied to the tip second end and, thus, when the tip second end is applied against an obstructed body cavity opening, the vibration acts to break up the obstruction and the suction contemporaneously acts to withdraw the accumulated fluid from the body cavity.

The body cavity can comprise a eustachian tube and the opening can comprise an opening in the nasopharynx region of a human throat. The tip can have a curved portion therein between the first and second ends therein. The second end of the tip can be positioned transversely with respect to the first end of the tip. A valve can be provided for controlling the flow of fluid through the longitudinal conduits of the tip and the housing.

In another aspect, the invention relates to a method for clearing obstructions in a body cavity opening behind which a volume of fluid has been accumulated comprising: applying mechanical vibration to the obstructed body cavity opening to reopen the body cavity opening; and applying suction to the obstructed body cavity opening generally contemporaneously with the vibration application step to withdraw fluid that has accumulated behind the obstruction.

The step of applying vibration and the step of applying suction can be performed by a single device. The body cavity can comprise a eustachian tube and the opening comprises an opening in the nasopharynx region of a human throat. A housing can have a longitudinal internal conduit, the internal conduit can terminate at a first end and a second end, the first and second ends can have attachment portions thereon, the attachment portion at the first end can be adapted to be interconnected to a suction source; a motor can be mechanically interconnected to the second end attachment portion and adapted to impart vibratory movement to the second end attachment portion; an elongated tip having a first end and a second end, each of the first and second ends can have an opening therein, the tip having a longitudinal internal conduit extending between the openings in the first and second ends of the tip, the first end of the tip being mounted to the attachment portion at the housing second end wherein the internal conduit of the tip is in fluid communication with the longitudinal conduit of the housing; whereby actuation of the motor imparts vibratory movement to the second end attachment portion, and thereby to the attached tip and, when the housing first attachment portion is interconnected to a suction source, suction and vibration are simultaneously applied to the tip second end and, thus, when the tip second end is applied against an obstructed body cavity opening, the vibration acts to break up the obstruction and the suction contemporaneously acts to withdraw the accumulated fluid from the body cavity.

Other objects, features, and advantages of the invention will be apparent from the ensuing description in conjunction with the accompanying drawings.

DETAILED DESCRIPTION

Figure 1:
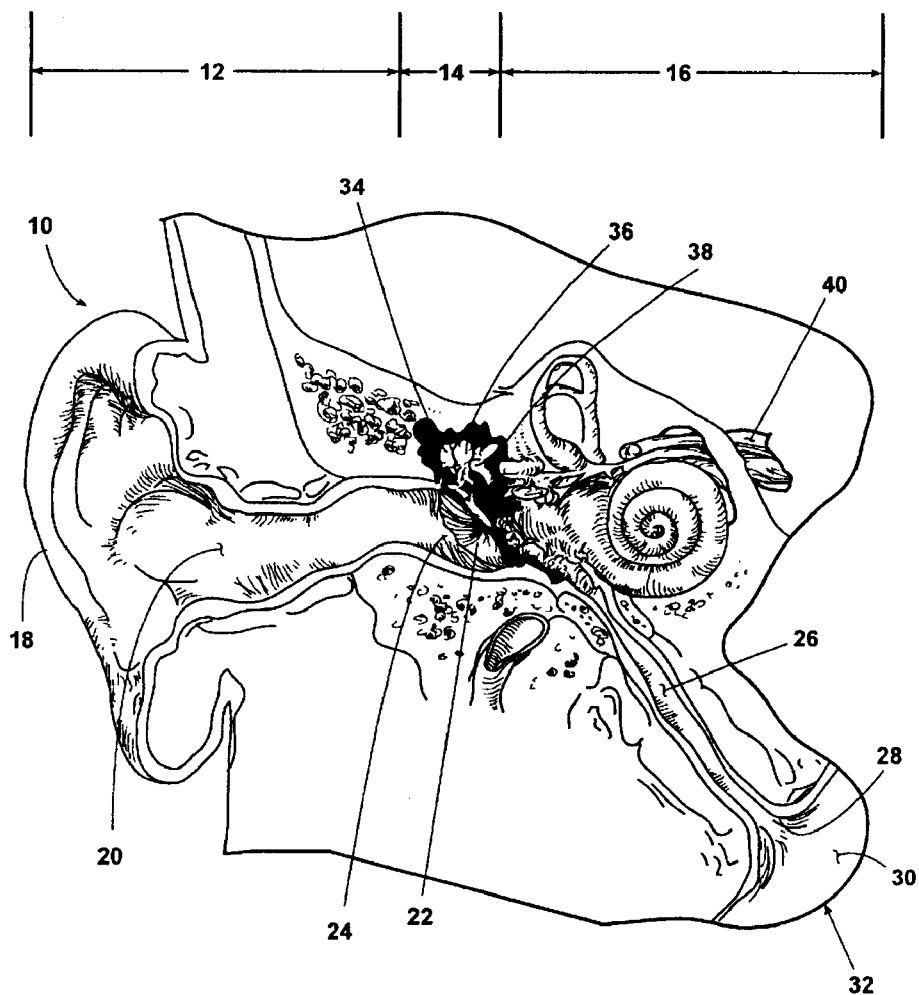
FIG. 1 is a cross section of a human ear showing the inner, middle and outer ear portions and the eustachian tube connecting the middle ear with the nasopharynx region of the throat via a distal opening thereof.
Figure 2:
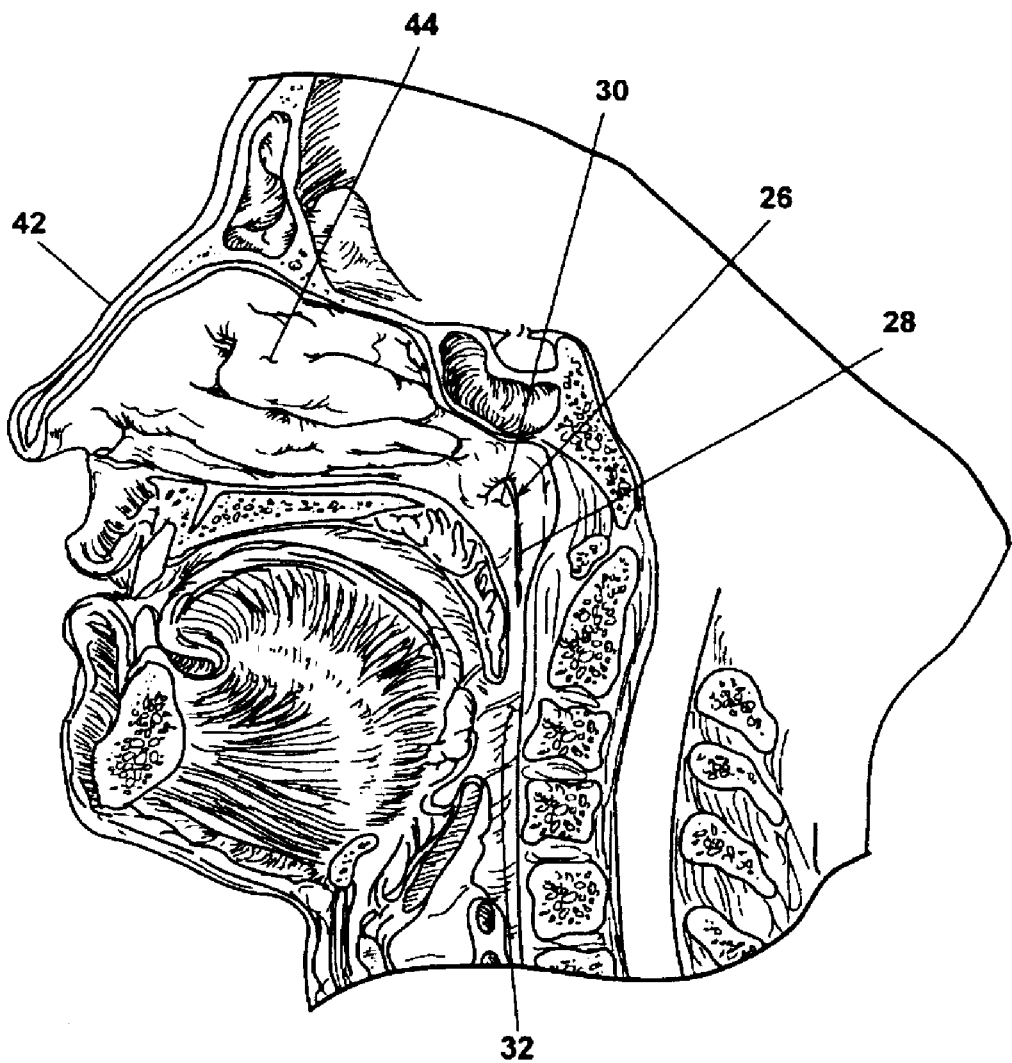
FIG. 2 is a cross section of a human head showing the nasopharynx region of the throat illustrated in FIG. 1 containing the distal opening of the eustachian tube illustrated in FIG. 1.
Figure 3:
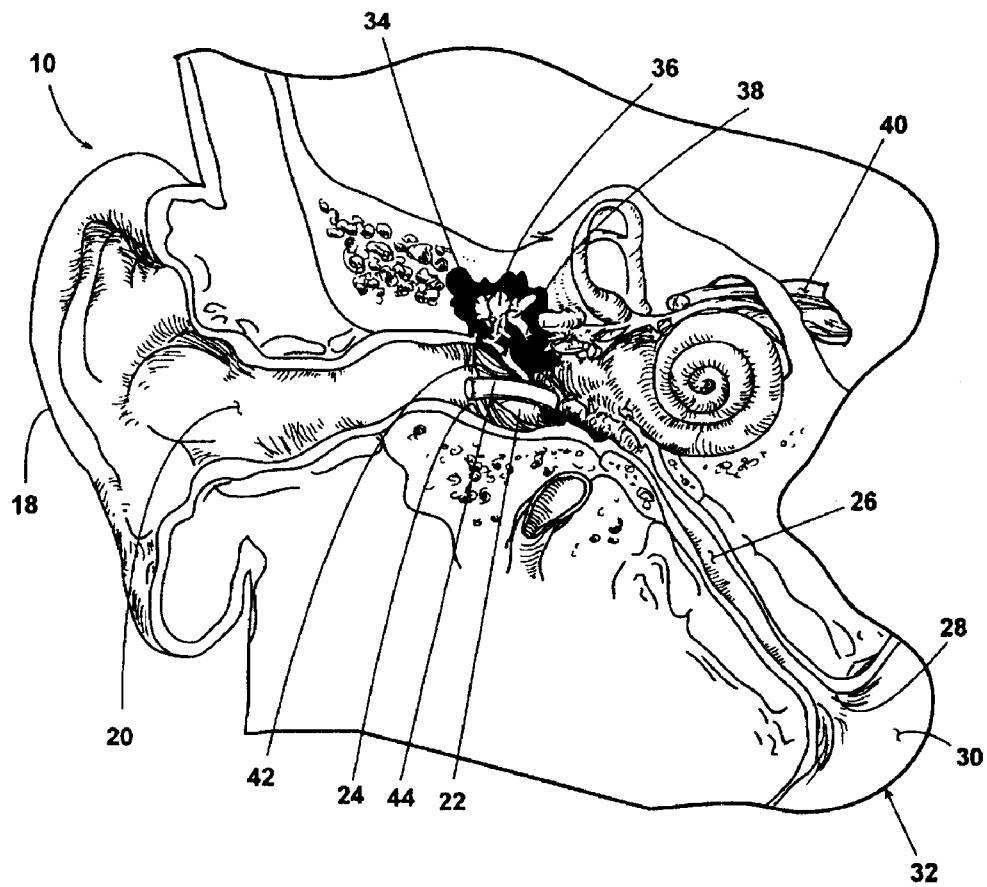
FIG. 3 is a cross section of a human ear in the orientation shown in FIG. 1 showing a prior art surgical method for relieving fluid in the middle ear in which a ventilation tube is lodged within an incision in the eardrum.
Figure 4:
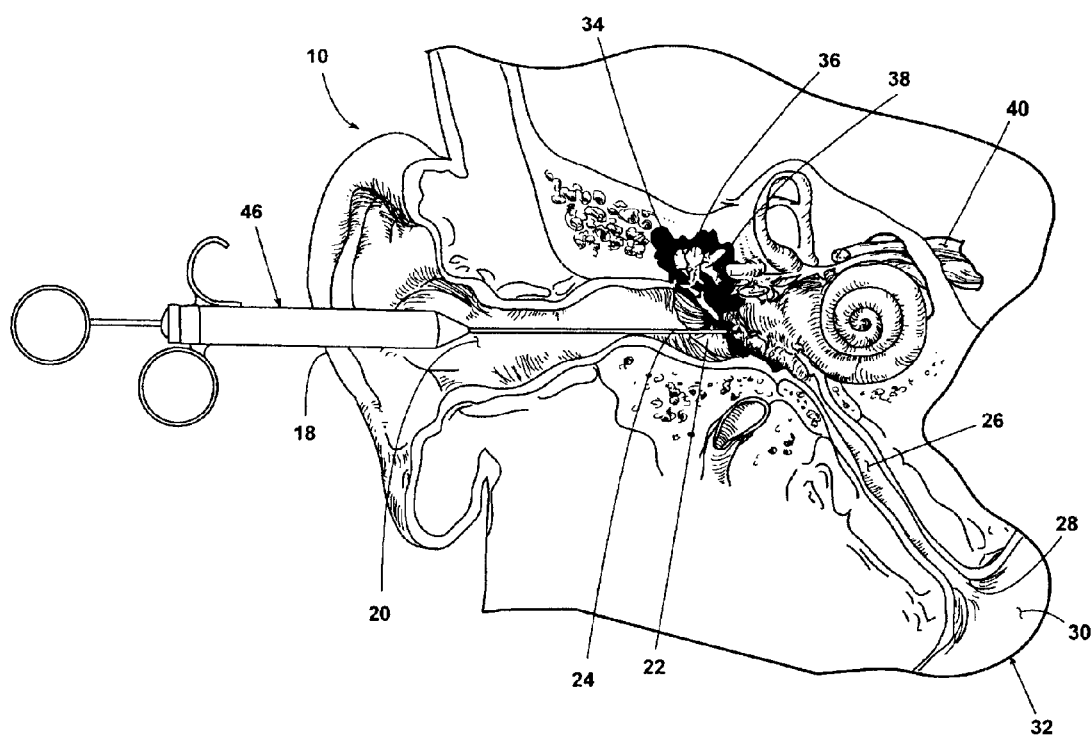
FIG. 4 is a cross section of a human ear in the orientation shown in FIG. 1 showing a prior art surgical method for relieving fluid in the middle ear in which a syringe is shown having a needle perforating the eardrum.
Figure 5:
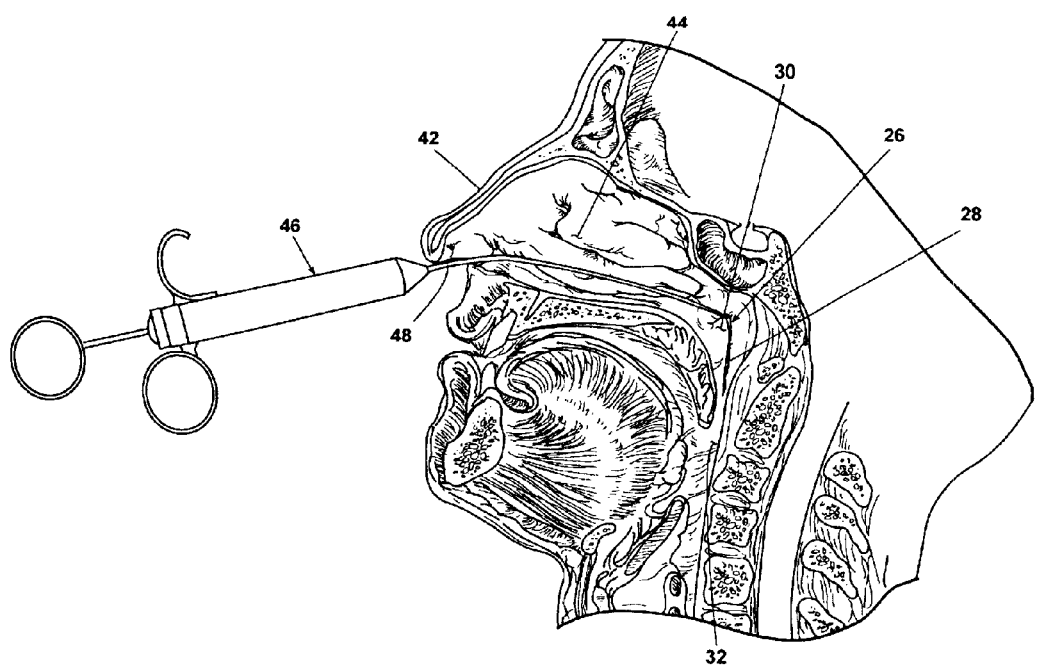
FIGS. 5–6 show a cross section of a human head in the orientation shown in FIG. 2 showing a prior art politzeration method for relieving fluid in the middle ear in which a syringe is shown having a flexible tip extending into the nose and/or throat area so that the tip abuts the distal opening of the eustachian tube while the nose is plugged.
Figure 6:
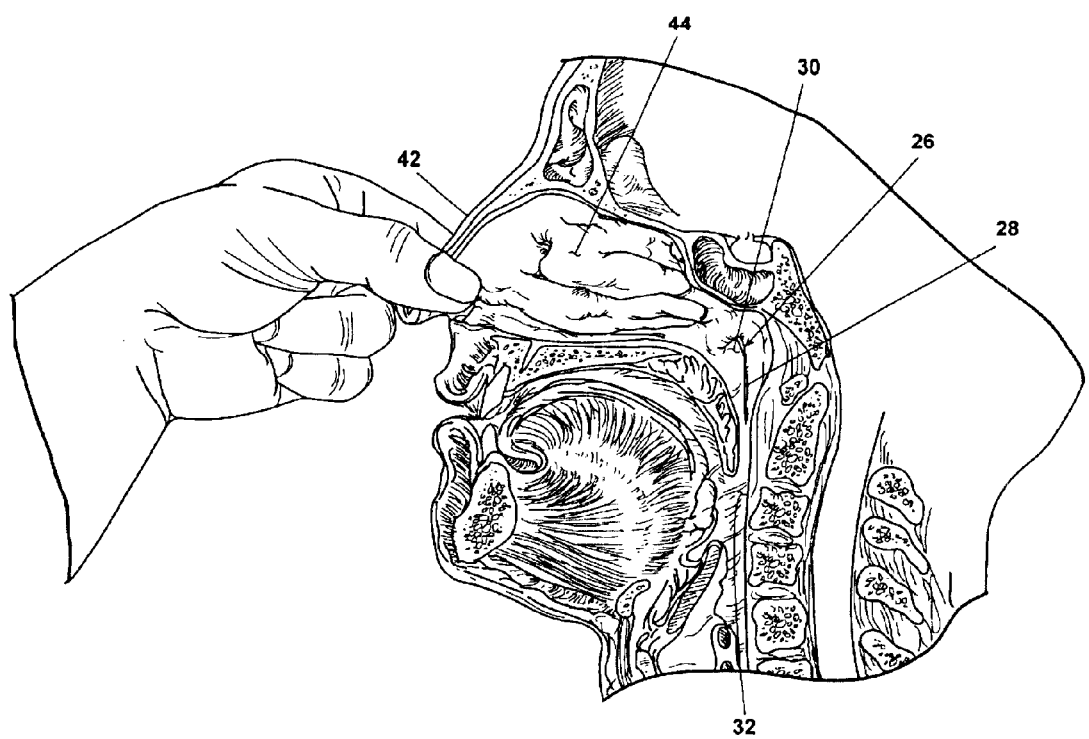
Figure 7:
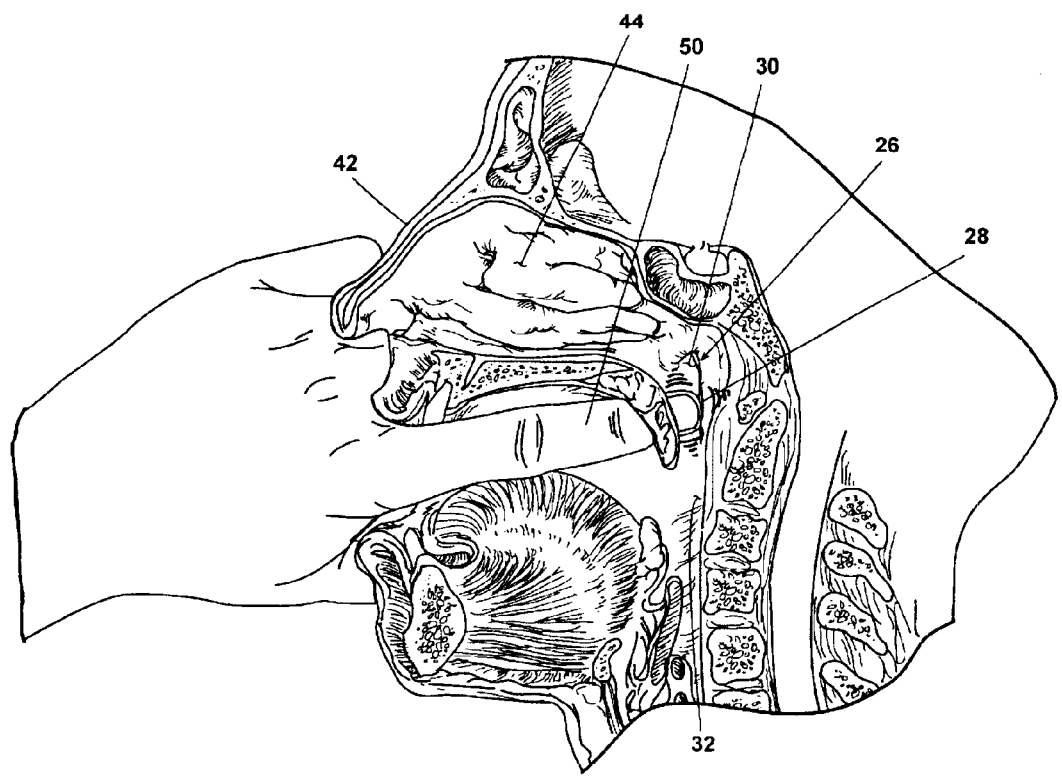
FIG. 7 is a cross section of a human head in the orientation shown in FIG. 2 showing a prior art alternative medicine method for relieving fluid in the middle ear in which a physician's finger massages the distal opening of the eustachian tube.
Figure 8:
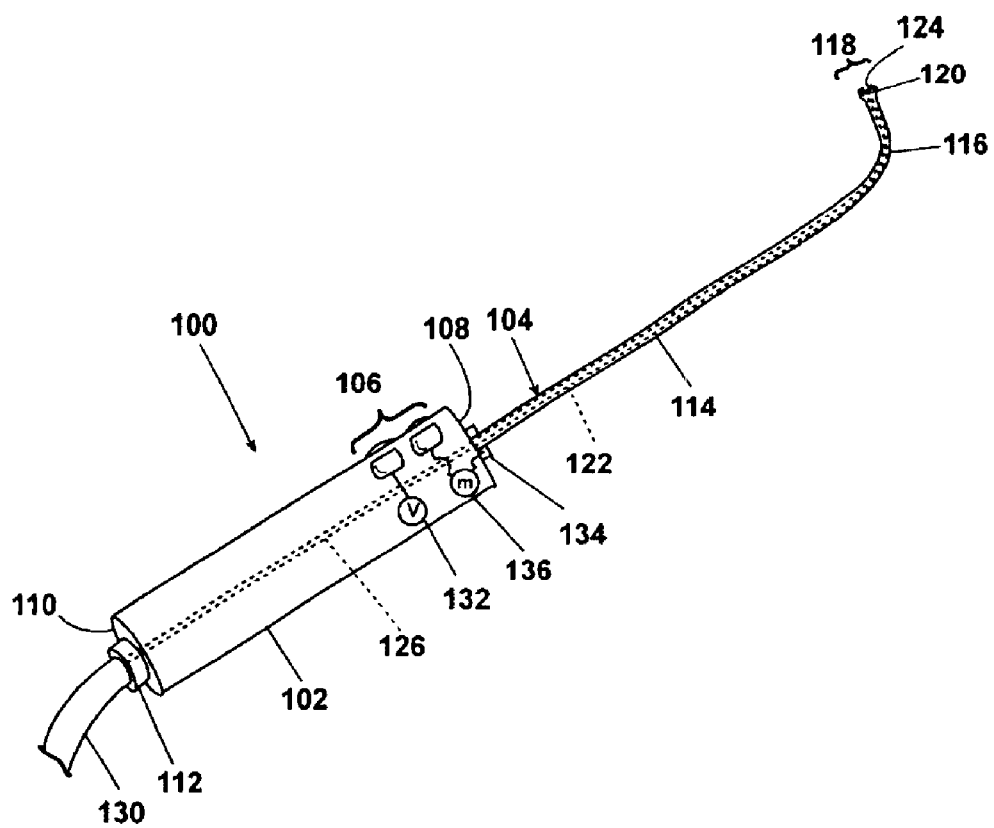
FIG. 8 is a device for simultaneously applying vibration to a blocked eustachian tube via a tip thereon while suctioning fluids accumulated therein through the tip according to the present invention.
Figure 9:
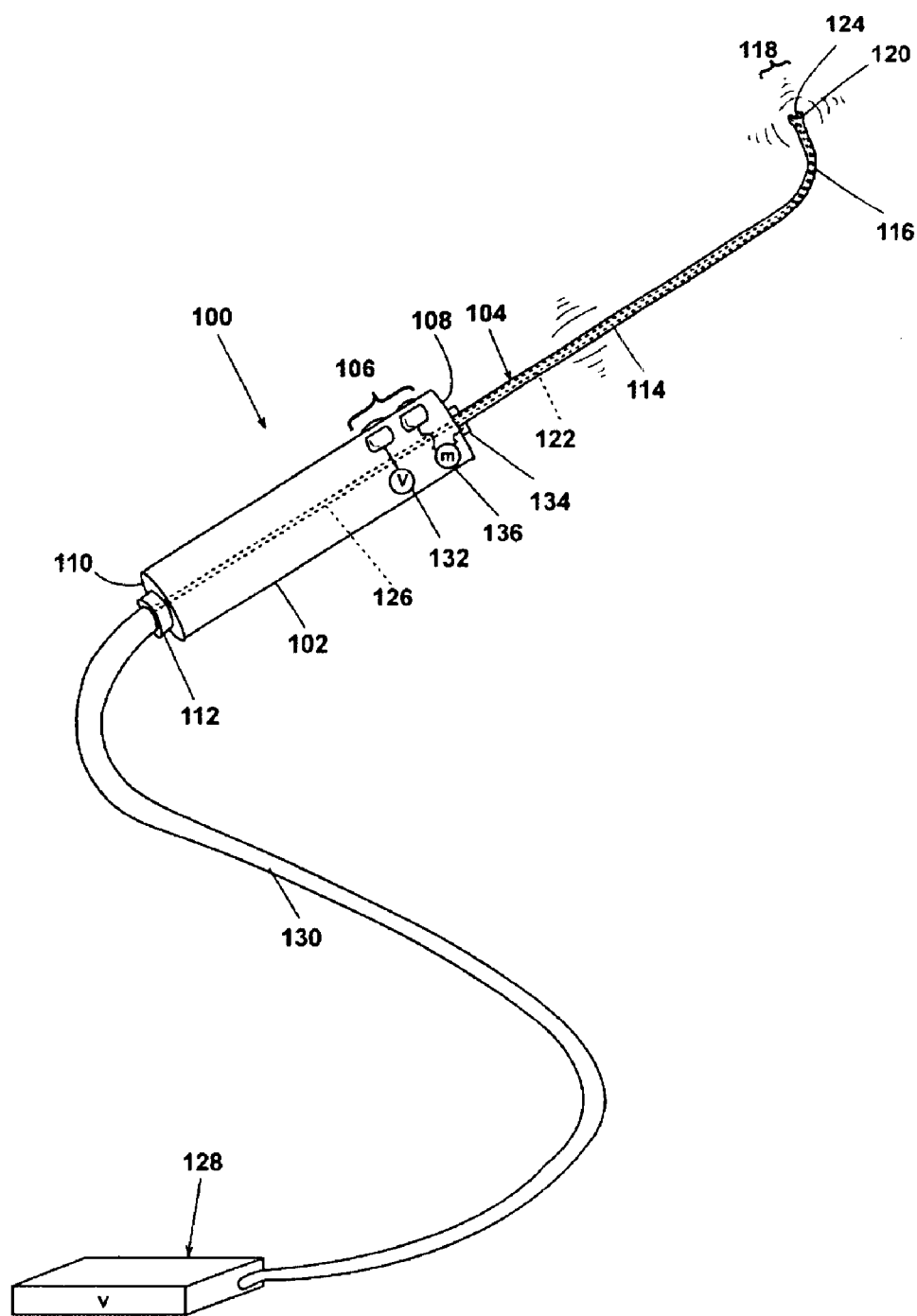
FIG. 9 is the device illustrated in FIG. 8 showing the device interconnected to a medical suction source and a motor that provides vibration to the tip of the device for applying the vibration to the blocked eustachian tube opening.

Referring now to FIGS. 8–11 and to FIGS. 8–9 in particular, a device 100 is shown comprising a housing 102 having an elongated tip 104 extending therefrom. The device 100 overcomes the limitations of prior art methods of relieving fluid accumulation in the middle ear by simultaneously applying vibration to a blocked eustachian tube via the tip 104 thereon while suctioning fluids accumulated therein through the tip 104.

The housing 102 of the device 100 comprises an elongated member adapted to be grasped by a user, such as a medical doctor or alternative medicine practitioner. The housing 102 can be provided with a control panel 106 having one or more buttons thereon for controlling various features of the device 100. For example, one button on the control panel 106 can be a conventional power switch, another button can selectively interconnect a suction source to the tip 104, another button can actuate a spray nozzle (not shown) to apply an anesthetic spray from an end of the housing 102, another button can actuate a light directly attached to or adjacent the housing 102 to direct light toward the end of the tip 104 to assist the user in viewing the interior of the patient's mouth. The housing 102 has a first end 108 onto which the tip 104 is attached and a second end 110 onto which a conduit attachment 112 is mounted.

The tip 104 is a resilient, flexible member having an elongated portion 114 attached at one end to the first end 108 of the housing 102 and terminating at a second end in a transversely-curved portion 116. The curved portion 116, in turn, preferably terminates in a distal end 118 having a textured surface 120. The textured surface 120 preferably has a knurled, knobby, or otherwise continuous or discontinuous pattern of indentations and protrusions adapted to increase friction and agitate a surface against which the textured surface 120 is abutted.

The tip 104 further has an internal longitudinal conduit 122 extending from an opening 124 in the textured surface 120 of the distal end 118 of the tip to the interconnection with the first end 108 of the housing 102. The longitudinal conduit 122 is then fluidly interconnected to a second longitudinal conduit 126 extending through the housing 102 and terminating at the second end 110 thereof. The longitudinal conduit 126 of the housing 102 is also fluidly interconnected with the conduit attachment 112. The conduit attachment 112 is any of many well-known devices for attachment of a flexible conduit to a housing such as a quick-connect mounting nut, a threaded nut which threads onto a threaded shaft on the housing, etc.

The device 100 is adapted, via the conduit attachment 112, to be fluidly interconnected to a well-known source of suction for medical purposes, such as a vacuum 128, via a length of tubing 130 as shown in FIG. 9. A selective actuator for selectively interconnecting the vacuum 128 with the opening 124 in the distal end 118 of the tip 104, such as a valve 132, can be provided on any of the vacuum 128, tubing 130, or the first or second longitudinal conduits 122 and 126, respectively. Preferably, the valve 132 is provided on the longitudinal conduit 126 in the housing 102 and is interconnected to an actuator on the control panel 106 so that the user can selectively control the application of suction to the opening 124 on the distal end 118 of the tip 104. It will also be understood that the device 100 can be attached to a conventional medical suction unit that is well known in the art.

Preferably, the tip 104 is releasably interconnected to the housing 102 by a mounting flange 134. This releasable mounting of the tip 104 to the housing 102 provides several benefits among which are maintaining sterility in the operation of the device since the tip 104 can thereby be provided as a single-use member that can be disposed after use. The mounting flange 134 is preferably mechanically interconnected to a motor 136 via a conventional mechanism adapted to convert motion provided by the motor 136 into vibratory articulation of the tip 104, and preferably vibratory articulation of the distal end 118 of the tip 104. It will be understood that the motor 136 can be operably interconnected to the control panel 106 for selective operation of the motor 136, and thereby the selective application of vibration to the tip 104.

The tip 104 is preferably a single-use disposable member made from a resilient synthetic resin material and preferably has sufficient rigidity to allow the user to abut the distal end 118 of the tip 104 against an obstructed body cavity opening, such as an obstructed eustachian tube opening 28. The curved portion 116 of the tip 104 permits the user to extend and navigate the distal end 118 of the tip 104 to the obstructed eustachian tube opening 28 through the patient's mouth and to the nasopharynx region 30 in the patient's throat 32. The tip 104 can be either disposable or non-disposable and can be made in different sizes to adapt the device 100 to be equally usable with children patients as well as adults. The textured surface 120 on the distal end 118 of the tip 104 increases the friction when the user contacts the distal end 118 of the tip 104 against the obstruction in the opening 28 of the eustachian tube 26.

The control panel 106 on the housing 102 permits the user to conveniently control the suction, lighting, a spray device for medications/anesthetics, visualization, and the motor for the vibration. The housing 102 can be provided without the control panel 106 and controlled via controls on an attached medical suction unit, such as the vacuum 128. Of course, if only suction is required, the medical suction device can be interconnected directly to the inventive tip 104 described herein without need for the housing 102. Further, the housing 102 and tip 104 can be employed without attachment to the medical suction device, if no suction is required and vibration is only needed for application to the obstructed opening 28 of the eustachian tube 26.

Figure 10:
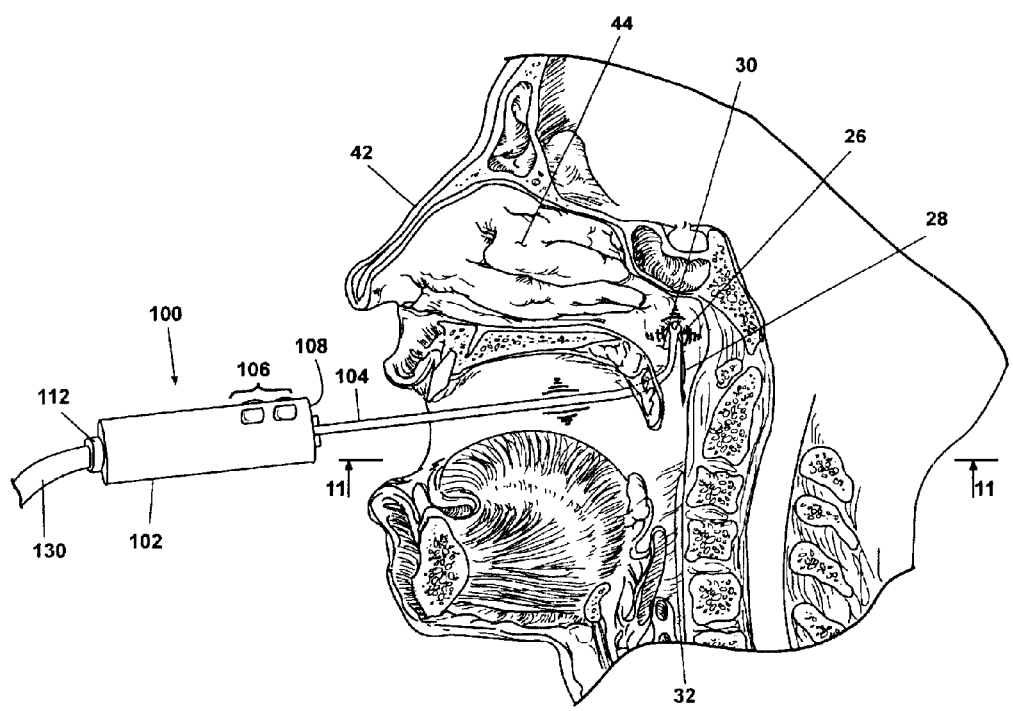
FIG. 10 is a cross section of a human head in the orientation shown in FIG. 2 wherein the device of FIGS. 8–9 has been inserted into the patient's mouth so that the tip is positioned against the eustachian tube opening in the nasopharynx region of the throat and applies vibration and suction thereto.
Figure 11:
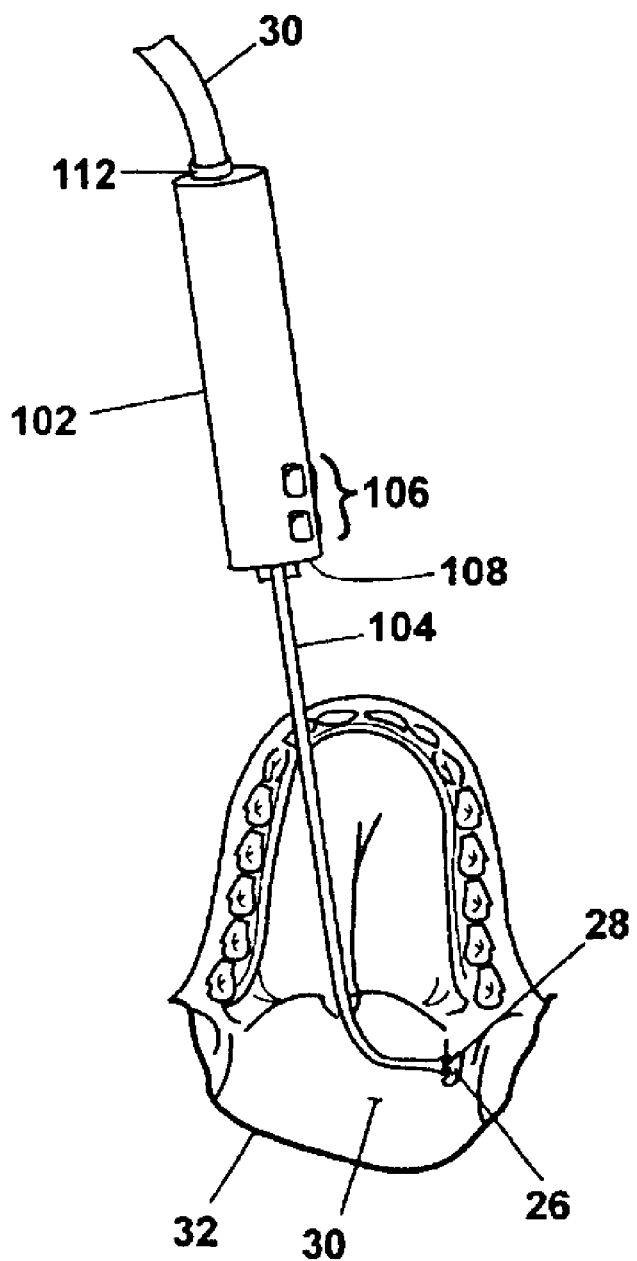
FIG. 11 is a cross sectional view taken along lines 11—11 of FIG. 10 also illustrating the positioning of the tip of the device of FIGS. 8–9 against the eustachian tube opening according to the invention.

The use of the device 100 according to the invention is shown in greater detail in FIGS. 10–11 which show the device 100 being inserted into a patient's mouth so that the tip 104 is positioned against the obstructed opening 28 of the eustachian tube 26 in the nasopharynx region 30 of the throat 32. It will be understood that anesthetic can preferably by either sprayed into the nasopharynx region 30 of the throat 32 contemporaneously with the insertion of the device 100 into the patient's mouth or prior to insertion, although the use of an anesthetic is not necessary or critical to the description of this inventive device and method.

The inventive method consists of inserting the device 100, with or without a pre-spray of topical anesthesia, through the patient's open mouth and into the nasopharynx region 30 of the throat 32. With the help of the curved portion 116 in the tip 104, the distal end 118 of the tip 104 of the device 100 can be placed against or adjacent to the opening 28 of the eustachian tube 26. Known optic positioning cameras or scopes can be employed to further aid the user in locating and positioning the tip 104 into place adjacent to the obstructed eustachian tube 26.

Once the device 100 is in position (i.e., the distal end 118 of the tip 104 is positioned adjacent or on the opening 28 of the obstructed eustachian tube 26), treatment consists of either suction of secretions, or vibration, or both. The user can actuate the motor 136 to apply vibratory articulation and movement to the distal end 118 of the tip 104. Simultaneously, the user can actuate the vacuum 128 (such as by actuating the valve 132), to suction any fluids released by the vibratory action of the tip 104 against the opening 28 of the eustachian tube 26.

This method can be performed for a predetermined amount of time and repeated as necessary. As the opening 28 of the eustachian tube 26 begins functioning properly, suction can be further applied by the tip 104 (as interconnected to the vacuum 128) directly into the eustachian tube 26 via the opening 28 to clear the serous fluid there, or the fluid may be allowed to drain freely. At any time during the method or afterwards, medications may be sprayed directly onto the walls of the nasophayrnx 30 or on the opening 28 of the eustachian tube 26. This method is better than previous technology because it is more effective at opening the eustachian tube 26 and collecting and removing fluid accumulation therein.

While the invention has been specifically described in connection with certain specific embodiments thereof, it is to be understood that this is by way of illustration and not of limitation, and the scope of the appended claims should be construed as broadly as the prior art will permit.

What is claimed is:

1. A method for clearing an obstruction in an eustachian tube opening in the nasopharynx region of a human throat behind which a volume of fluid has accumulated within a eustachian tube, such as during an infection of the middle ear, comprising the steps of:

vibrating the nasopharynx region in the area of the eustachian tube opening to at least one of break up and dislodge the obstruction without permanent damage to the eustachian tube opening; and removing the fluid within the eustachian tube accumulated behind the obstruction through the eustachian tube opening in association with the vibrating step;

wherein the vibrating step and the removing step are performed by a device comprising a housing having a longitudinal internal conduit, the internal conduit terminating at a first end and a second end, the first and second ends having attachment portions thereon, the attachment portion at the first end being adapted to be interconnected to a suction source; a motor mechanically interconnected to the second end attachment portion and adapted to impart vibratory movement to the second end attachment portion; an elongated tip having a first end and a second end, each of the first and second ends having an opening therein, the tip having a longitudinal internal conduit extending between the openings in the first and second ends of the tip, the first end of the tip being mounted to the attachment portion at the housing second end wherein the internal conduit of the tip is in fluid communication with the longitudinal conduit of the housing; whereby actuation of the motor imparts vibratory movement to the second end attachment portion, and thereby to the attached tip and, when the housing first attachment portion is interconnected to a suction source, suction and vibration are simultaneously applied to the tip second end and, thus, when the tip second end is applied against an obstructed body cavity opening, the vibration acts to break up the obstruction and the suction contemporaneously acts to withdraw the accumulated fluid from the eustachian tube opening;

whereby, once the vibrating step has reduced the obstruction in the eustachian tube opening, the removing step withdraws the fluid from within the eustachian tube to relieve pain and discomfort associated with the fluid accumulation.

2. The method of claim 1 and further comprising the step of positioning a portion of the device over the eustachian tube opening prior to the vibrating and removing steps.

3. The method of claim 2 wherein the device includes a curved tip for facilitating placement of the device over the eustachian tube opening and avoiding protrusions in the nasopharynx region.

* * * * *